(12) United States Patent
Erhan et al.

(10) Patent No.: US 8,173,825 B2
(45) Date of Patent: May 8, 2012

(54) METHOD OF MAKING FATTY ACID ESTER DERIVATIVES

(75) Inventors: Sevim Z. Erhan, Peoria, IL (US); Kenneth M. Doll, Peoria, IL (US); Brajendra K. Sharma, Peoria, IL (US)

(73) Assignees: The United States of America, as represented by the Secretary of Agriculture, Washington, DC (US); The Penn State Research Foundation, University Park, PA (US)

( * ) Notice: Subject to any disclaimer, the term of this patent is extended or adjusted under 35 U.S.C. 154(b) by 797 days.

(21) Appl. No.: 11/717,524

(22) Filed: Mar. 13, 2007

(65) Prior Publication Data

US 2008/0154053 A1      Jun. 26, 2008

Related U.S. Application Data

(60) Provisional application No. 60/875,960, filed on Dec. 20, 2006.

(51) Int. Cl.
*C07C 51/00*       (2006.01)
(52) U.S. Cl. ....................................... 554/149; 554/213
(58) Field of Classification Search ................... 554/149, 554/213
See application file for complete search history.

(56) References Cited

U.S. PATENT DOCUMENTS

| 4,171,420 A * | 10/1979 | Doorakian et al. ............. 528/89 |
| 6,274,750 B1 * | 8/2001 | Sato et al. ...................... 554/213 |
| 6,583,302 B1 | 6/2003 | Erhan et al. |
| 2006/0264568 A1 * | 11/2006 | Pajerski ........................ 524/591 |

FOREIGN PATENT DOCUMENTS

WO      WO 2006014483 A2 *    2/2006

OTHER PUBLICATIONS

Pages-Xatart-Pares,Xavier,et al.,Synthesis of New Deriv. From Veg. Oil . . . Epoxidatn & Oxirane Opening,Rec.Dvlpmnts in Synthesis of Fatty Acd Derivatives,p. 141-156,1999,AOCS Pres.

* cited by examiner

*Primary Examiner* — Deborah D Carr
(74) *Attorney, Agent, or Firm* — John Fado; Randall E. Deck; Lesley Shaw

(57) ABSTRACT

Fatty acid ester derivatives and a process for their production from unsaturated fatty acids are disclosed. The process comprises:

a) reacting an unsaturated fatty acid or an ester thereof having one or more sites of unsaturation, with an epoxidation reagent to form a fatty acid epoxide wherein at least one of the sites of unsaturation of the fatty acid or fatty acid ester is converted to an oxirane ring; and b) reacting the fatty acid epoxide produced in a) with a carboxylic acid to form a hydroxy fatty acid ester derivative wherein the oxirane ring is opened and converted to a hydroxy ester comprising a hydroxyl group at one carbon of the opened oxirane ring and an ester of the carboxylic acid at the other carbon of the opened oxirane ring.

13 Claims, 13 Drawing Sheets

METHOD OF MAKING FATTY ACID ESTER DERIVATIVES

CROSS-REFERENCE TO RELATED APPLICATION

This application claims the benefit under 35 U.S.C. 1.19(e) of U.S. provisional No. 60/875,960, filed Dec. 20, 2006, the contents of which are incorporated by reference herein.

BACKGROUND OF THE INVENTION

1. Field of the Invention

The Invention relates to novel fatty acid ester derivatives and a process of making the same.

2. Description of the Prior Art

The need to utilize bio-based resources is especially important considering the high cost of petroleum.[1,2] Of particular interest is the synthesis of branched oleochemicals which are being studied in the lubricant,[3-9] surfactant,[10-12] and fuel additive[13] industries. It has been shown that changing the structure of the alkyl chain has a large effect on the physical properties, such as cloud point[14] and the hydrophilic lipophylic balance (HLB), of the oleochemical. These changes can significantly increase the performance of a surfactant or lubricant material. For example, a branching in the fatty chain will increase hydrophobic area giving a lower HLB dramatically changing surface active properties.[15] These oleochemical products are good candidates for water in oil emulsifiers.[16-18] The improvement of lubricity properties of triglycerides upon the introduction of branching have also been demonstrated.[3]

One useful reaction for the modification of oleochemicals has been epoxidation. The epoxidation method of oleochemicals has been known for many years[19,20] and the process has been studied[21] and patented.[22] Epoxidized soybean oil (ESO) and natural rubber epoxide[23,24] have been studied, and ESO is commercially available and is widely used as a plasticizer. Oleochemical epoxides have also been used to synthesize polymer composites[25-29] and limited studies on the conversion of terminal epoxides to surfactants has also been performed.[30,31]

However, despite these advances the need remains for improved bio-based compounds effective as lubricants, surfactants, and/or fuel additives.

SUMMARY OF THE INVENTION

We have now discovered a new process for making fatty acid ester derivatives from unsaturated fatty acids which may be free or esterified, in high yields and under mild conditions. The process comprises:
a) reacting an unsaturated fatty acid or an ester thereof having one or more sites of unsaturation, with an epoxidation reagent to form a fatty acid epoxide wherein at least one of the sites of unsaturation of the fatty acid or fatty acid ester is converted to an oxirane ring; and
b) reacting the fatty acid epoxide produced in a) with a carboxylic acid to form a hydroxy fatty acid ester derivative wherein the oxirane ring is opened and converted to a hydroxy ester comprising a hydroxyl group at one carbon of the opened oxirane ring and an ester of the carboxylic acid at the other carbon of the opened oxirane ring. Alternatively, the fatty acid ester derivatives may be produced directly from commercially available epoxidized fatty acids or their esters, thereby rendering the first, epoxidation reaction unnecessary. Using this process we have also produced novel hydroxy oleic acid esters (stearic acid esters) of the formula:

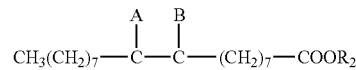

wherein $R_2$ is selected from the group of H, branched or straight chain alkyl groups, aromatic containing groups, and glycerides, and A and B are selected from the group of a hydroxyl group and R—COO—, with the proviso that when one is the hydroxyl group the other is the R—COO—.

In accordance with this discovery, it is an object of this invention to provide a method of making hydroxy fatty acid ester derivatives from free unsaturated fatty acids or their esters.

It is another object of this invention to provide a method of making hydroxy fatty acid ester derivatives under mild conditions and in high yield without the use of a catalyst.

Still another object of this invention is to provide a method of making hydroxy fatty acid ester derivatives from natural fatty acids and oils using environmentally friendly reagents.

Yet another object of this invention is to provide novel hydroxy oleic acid ester derivatives effective as lubricants, surfactants, and/or fuel additives.

Other objects and advantages of this invention will become readily apparent from the ensuing description.

DETAILED DESCRIPTION OF THE INVENTION

Figure 1:
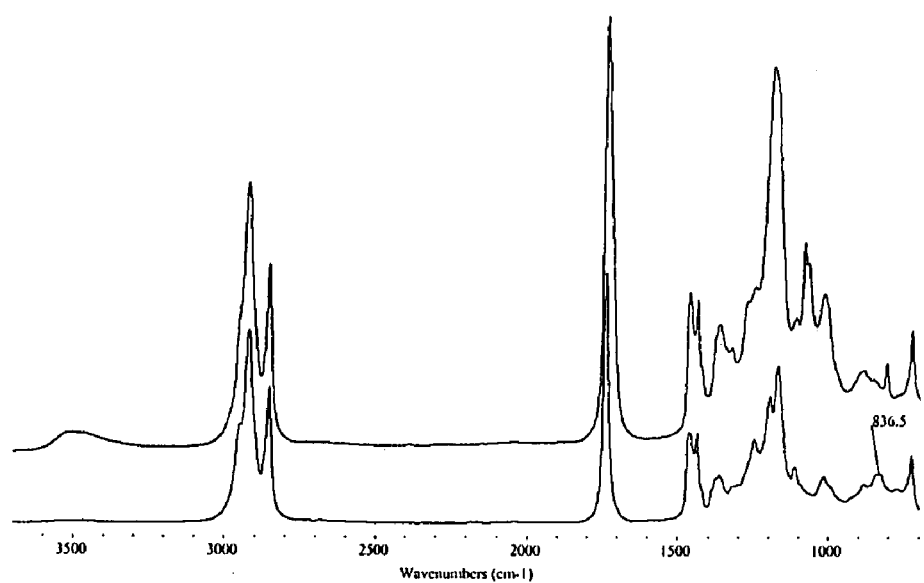
FIG. 1 shows the FTIR spectra of the propionic ester of methyl hydroxy-oleate (PMO) (top) from epoxidized methyl oleate (EMO) (bottom) from Example 1. The reaction progress can be judged by the loss of the EMO epoxide band at 837 cm$^{-1}$ and the appearance of a broad OH band at ~3500 cm$^{-1}$, as well as the relative growth of the of the carbonyl ester band at ~1740 cm$^{-1}$.
Figure 2:
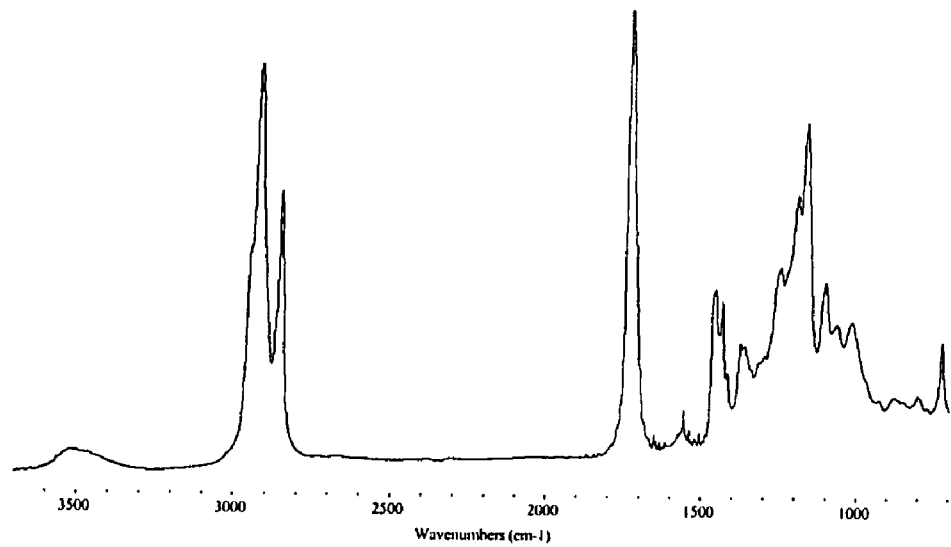
FIG. 2 shows the FTIR spectra of octanoic ester of methyl hydroxy-oleate (OMO) from Example 1. The product displays a large carbonyl frequency at 1738 cm$^{-1}$ as well as a broad OH band at ~3500 cm$^{-1}$.
Figure 3:
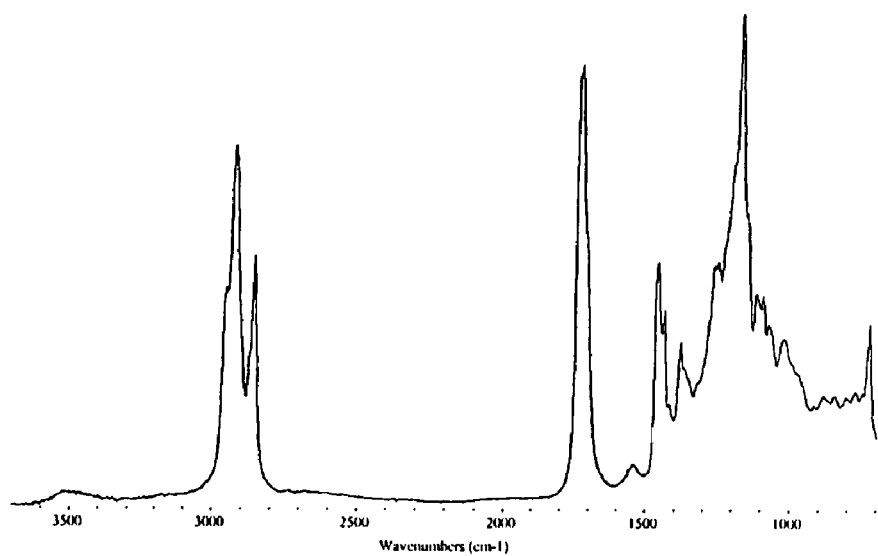
FIG. 3 shows the FTIR spectra of 2-ethyl hexyl ester of methyl hydroxy-oleate (2-EHMO) from Example 1. The product displays a large carbonyl frequency at 1732 cm$^{-1}$ as well as a broad OH band at ~3500 cm$^{31\ 1}$.
Figure 4:
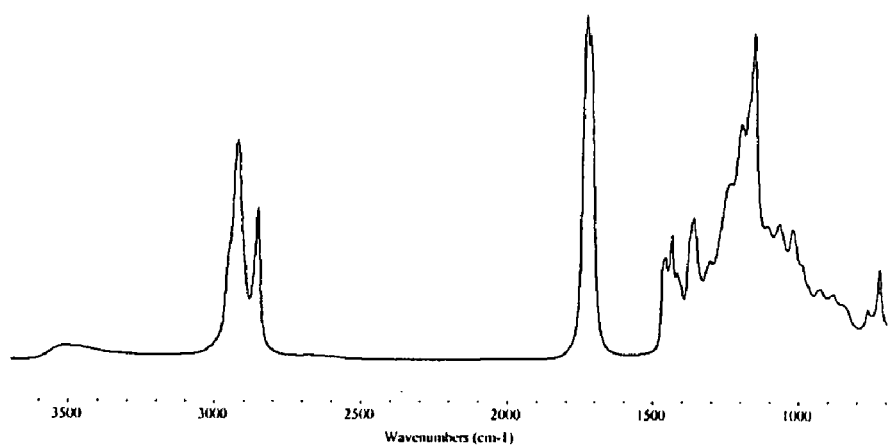
FIG. 4 shows the FTIR spectra of levulinic ester of methyl hydroxy-oleate (LMO) from Example 1. The product displays a large carbonyl frequency at 1736 cm$^{-1}$ as well as a broad OH band at ~3500 cm$^{-1}$. Additionally, there is also an overlapping resonance in the carbonyl region at ~1719 cm$^{-1}$ corresponding to the ketone moiety in the product.

Using the process of this invention, fatty acid ester derivatives may be formed from a variety of unsaturated fatty acids (olefins). The starting unsaturated fatty acid is not critical, and any $\Delta^3$ to $\Delta^{17}$ unsaturated fatty acid (i.e. having a double bond between $\Delta^3$ and $\Delta^{17}$ inclusive) containing from 4 to 30 carbon atoms or longer may be used. Thus, starting fatty acids include fatty acids of the formula $R_1$—$COOR_2$ wherein $R_1$ is a straight or branched chain olefin, and $R_2$ is H, branched or straight chain alkyl or alkenyl groups, aromatic containing groups, or glycerides (mono-, di- or triglyceride). Preferred starting fatty acids include, but are not limited to free and esterified, unsaturated $\Delta^3$ to $\Delta^{17}$ unsaturated fatty acid containing from 4 to 22 carbon atoms, more particularly free and esterified unsaturated $\Delta^3$ to $\Delta^{17}$ unsaturated fatty acid containing from 8 to 22 carbon atoms, and most particularly free and esterified unsaturated $\Delta^9$ to $\Delta^{15}$ unsaturated fatty acid containing from 8 to 22 carbon atoms. Examples of particularly preferred unsaturated fatty acids which may be used herein include free and esterified palmitoleic acid (16:1 $\Delta^9$), oleic acid (18:1 $\Delta^9$), linoleic acid (18:2, $\Delta^{9,12}$), erucic acid (22:1, $\Delta^{13}$), and linolenic acid (18:3, $\Delta^{9,12,15}$), 5-eicosenoic acid (20:1, $\Delta^5$), 5-docosenoioc acid (22:1, $\Delta^5$), 5,13-docosadienoic acid (22:2, $\Delta^{5,13}$), petroselinic acid (16:1, $\Delta^6$), elaidic acid (18:1 $\Delta^9$), and trans isomers of any of the above.

Unsaturated fatty acids are naturally occurring in a variety of plant oils and may be conveniently obtained for use therefrom. Without being limited thereto, oils which may be used as sources, include soybean, cottonseed, corn, olive, peanut, palm, sesame, sunflower, canola, castor, safflower, linseed, oiticia, tung, rice, crambe, high erucic rape, and high oleic canola oils, with soybean oil being particularly preferred.

As starting materials in the reaction of the invention, the unsaturated fatty acids may be provided in substantially pure form or, in the alternative, they may be provided as a mixture or in impure form. Moreover, although the starting unsaturated fatty acids may be free acids, the reaction may also be conducted using fatty acids which are esterified with aliphatic alcohols such as methanol, ethanol, isopropanol, or branched chain alcohols such as 2-ethyl hexanol or Guerbet alcohols, or with glycerol as mono-, di- or triglycerides. Because fatty acids occur predominantly as triglycerides in plant oils, the above-mentioned naturally occurring oils may be used directly in the reaction, thereby foregoing the need for any preliminary fatty acid isolation of the oil.

The practitioner skilled in the art will of course recognize that for products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Once the starting material has been selected, the free or esterified unsaturated fatty acids are reacted under conditions and for a period of time effective to at least partially, but preferably completely, epoxidize the carbon/carbon double bonds therein. A variety techniques for the epoxidation of olefins are known in the art and are suitable for use herein. For example, without being limited thereto, suitable techniques include those described by Qureshi et al. (Polymer Science and Technology, Vol. 17, Plenum Press, p. 250), Croco et al. (U.S. Pat. No. 5,166,372), Nowak et al. (U.S. Pat. Nos. 6,740,763 or 6,734,315), and preferably Bunker and Wool (Synthesis and characterization of monomers and polymers for adhesives from methyl oleate. *J. Polym. Sci., Part A: Polym. Chem.* 2002, 40, 451-458), the contents of each of which are incorporated by reference herein. In accordance with the preferred embodiment, epoxidation is effected by reaction of the unsaturated fatty acid with a combination of a peroxide and a carboxylic acid or its anhydride, or by reaction with a peroxycarboxylic acid such as peroxy-benzoic acid. Suitable peroxides include hydrogen peroxide or any organic peroxides which will form a peracid with a carboxylic acid or it's anhydride. However, preferred epoxidation reagents include hydrogen peroxide with either formic acid, acetic acid, or acetic anhydride. The order of addition is not critical, and the peroxide and carboxylic acid may be combined prior reacting with the fatty acid, or they may be added separately to the fatty acid, or all of the peroxide, carboxylic acid, and fatty acid may be combined concurrently. The reaction is preferably conducted at low temperatures, more preferably between about 0° and about 30° C., most preferably between about 0° and about 25° C. Because the reaction is exothermic, the temperature is preferably controlled such as by cooling. Temperature control is particularly preferred when reacting free, non-esterified fatty acids to prevent reaction of the acid moiety and polymerization. In a particularly preferred embodiment reaction is initiated at a temperature of approximately 0° C. and maintained at this temperature for about 1 hour, before the temperature is allowed to increase to room temperature. The reaction is typically completed in approximately 3 to 6 hours.

As an alternative to producing the epoxidized fatty acids or their esters, it is understood that many of these same epoxidized fatty acids and fatty acid esters (e.g., glycerides) may be obtained in pure form or as mixtures from commercial sources. In this embodiment, the epoxidation reaction is thereby unnecessary and the invention may proceed directly with the esterification reaction described herein. The final products will of course be the same.

The fatty acid epoxide produced or otherwise obtained as described above is reacted with another carboxylic acid to form a hydroxy fatty acid ester derivative wherein the oxirane ring is opened and converted to a hydroxy ester comprising a hydroxyl group at one carbon of the opened oxirane ring and an ester of the carboxylic acid at the other carbon of the opened oxirane ring. The particular carboxylic acid in the reaction is not critical, and a variety of acids are suitable for use herein. When the carboxylic acid is represented by the formula R—COOH and the epoxidized fatty acid or an ester thereof having one or more oxirane rings is represented by the formula:

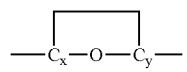

wherein x and y are consecutive integers, the hydroxy ester moieties generated from the oxirane rings of the epoxide may be represented by the formula:

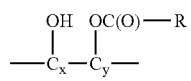

wherein R is a substituted or non-substituted cyclic, straight or branched chain hydrocarbon. Preferred carboxylic acids for use in this embodiment include, but not limited to, anhydrous C3 to C10 organic acids, particularly propionic, hexanoic, benzoic, octanoic or 2-ethyl hexanoic acid. Although the use of a solvent is optional, they are preferably not added. Rather, the carboxylic acid reactant is added in excess, and the acid itself will be effective as a solvent for the epoxide in the reaction. However, if the epoxide is not sufficiently miscible in the acid, such as may occur with acetic acid, a solvent such as an alcohol may be added. It is also envisioned that water and aqueous solvents may also be used. The reaction temperature is generally higher than that of the epoxidation reaction above. While not critical, the esterification reaction is preferably conducted at a temperature below about 120° C., most preferably below about 100° C. Reaction time may vary with temperature, and the reaction typically reaches completion in about 6 hours at 120° C. and about 24 hours at 88° C.

The use of a catalyst, including acid catalysts such as sulfuric acid, in the esterification reaction to produce the branched fatty acid esters from the epoxides is optional. However, the esterification reaction is preferably conducted in the absence of a catalyst, and particularly in the absence of added acid catalyst. Although addition of catalyst may increase the reaction rate, it's addition may also result in the production of dark-colored by-products Using the process described above with oleic acid as the starting material and R—COOH as the carboxylic acid, we have produced novel branched hydroxy oleic acid ester derivatives of the formula:

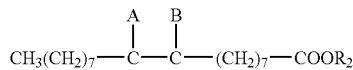

wherein $R_2$ is selected from the group of H, branched or straight chain alkyl groups, aromatic containing groups, and glycerides, and A and B are selected from the group of a hydroxyl group and R—COO—, with the proviso that when one is the hydroxyl group the other is the R—COO—.

In an alternate preferred embodiment, the esterification reaction May be practiced using a carboxylic acid which is substituted with a ketone or aldehyde moiety of the formula $R_3(O)$, and an acid catalyst such as sulfuric acid, phosphoric acid or tolene sulfonic acid is also added. In this embodiment, the above-mentioned hydroxy fatty acid ester derivative is formed as well as a fatty acid ketal wherein the oxirane is opened and converted to a to a ketal moiety. If the carboxylic acid is represented by the formula $R_3(O)COOH$, the oxirane ring of the epoxide is converted to a ketal group of the formula:

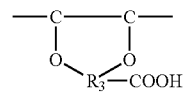

wherein $R_3$ may be the same as the R moiety of the carboxylic acid of the esterification reaction described above (cyclic, straight or branched chain hydrocarbons, and substituted cyclic, straight or branched chain hydrocarbons). For example, when reacting the epoxide with levulinic acid, the fatty acid ketal is of the formula:

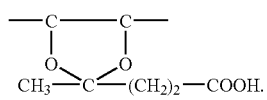

The relative amounts of the hydroxy fatty acid ester derivative and the fatty acid ketal may be altered or controlled by changing the temperature and catalyst concentration. As noted above, in the absence of catalyst the ketal is not formed. In contrast, the presence of catalyst and reduced reaction temperatures favors the production of the ketal.

The branched hydroxy fatty acid ester derivatives produced in accordance with this invention may be used as lubricants, surfactants, and/or fuel additives.

The following examples are intended only to further illustrate the invention and are not intended to limit the scope of the invention as defined by the claims.

EXAMPLE 1

A series of branched fatty esters utilizing carboxylic acids were synthesized, including: the levulinic ester of methyl hydroxy-oleate (LMO), the propionic ester of methyl hydroxy-oleate (PMO), the hexanoic ester of methyl hydroxy-oleate (HMO), the octanoic ester of methyl hydroxy-oleate (OMO), and the 2-ethyl hexyl ester of methyl hydroxy-oleate (2-EHMO). These specific acids have been selected to give a variety of different materials to study the effect of branch size and functionality.

Materials and Methods

Materials:
Methyl oleate (Sigma-Aldrich, St. Louis, Mo., Tech 70%), Hydrogen Peroxide (Sigma-Aldrich, St. Louis, Mo., A.C.S. Reagent, 30% Solution)), Formic Acid (Sigma-Aldrich, 96%, A.C.S. reagent), Hexanes (Sigma-Aldrich, St. Louis, Mo., >95%, HPLC grade), Acetone (Sigma-Aldrich, St. Louis, Mo., Chromasolve for HPLC, 99.9%), NaCl (Fisher, Fairlawn, N.J., A.C.S. Reagent), NaHCO$_3$ (Fisher, Fairlawn, N.J., A.C.S. Reagent), NaOH (Fisher, Fairlawn, N.J., A.C.S. Reagent), NaSO$_4$ (Sigma-Aldrich, St. Louis, Mo., 99+%, A.C.S. Reagent), Butanol (Fisher, Fairlawn, N.J., A.C.S. Reagent), Propionic acid (Sigma-Aldrich, St. Louis, Mo., 99.5%), Levulinic Acid (Sigma-Aldrich, St. Louis, Mo., 98%), Hexanoic Acid (Sigma-Aldrich, St. Louis, Mo., 99.5%), Octanoic Acid (Sigma-Aldrich, St. Louis, Mo., 99%), 2-ethyl-hexanoic acid (Sigma-Aldrich, St. Louis, Mo., 99%), Tetrabutylammonium Bromide (Sigma-Aldrich, St. Louis, Mo., 99%); Lithium Bromide (Sigma-Aldrich, St. Louis, Mo., 99+%), and Potassium Bromide (Buck Scientific, E. Norwalk, Conn.) were used as received.

Instrumentation and Equipment:

FTIR spectra of the starting material and products were recorded on a Thermonicolet (Madison, Wis.) Nexus 470 FTIR with a Smart ARK accessory containing a 45° ZeSe trough. Data was collected and processed on a Windows 2000 equipped Dell Optiplex GX260 pentium 4, 2.46 GHz computer running Omnic 6.2 software.

Gas chromatography was performed on a Hewlett Packard (Loveland, Colo.) 5890 GC system equipped with a 6890 series injector and an FID detector. A J and W DB-1 (15 m×320 um) was used with a helium flow rate of ~0.9 mL min$^{-1}$. The temperature program used started at 180° C. for two minutes then increased to 280° C. at 5° C. min$^{-1}$ and held for 5 min. Gas chromatography-Mass Spectrometry (GC-MS) was performed on a Hewlett Packard (Loveland, Colo.) 5890 GC series II plus system equipped with a 6890 series injector and a Hewlett Packard 5970 MSD detector in EI mode. A Supelco SPB-35 (30 m×320 um) was used with a helium flow rate of ~0.9 mL min$^{-1}$. The temperature program used started at 150° C. then increased to 290° C. at 10° C. min$^{-1}$. A 1 uL injection was used with a 70:1 split and an inlet temperature of 250° C. and a detector temperature of 280° C. HP-MS Chemstation software was used for data collection and processing.

NMR was performed on a Bruker (Boston, Mass.) Avance 500 NMR operating at 500 MHz for $^1$H and 125 MHz for $^{13}$C. Bruker Icon NMR software was used running on an HP x1100 Pentium 4 workstation. Peaks were referenced to sodium 3-trimethylsilylpropionate-2,2,3,3-$d_4$ (TSP) at 0.0000 ppm. Simulations of $^{13}$C NMR spectra were performed by ACD/Labs 6.00 ACD/CNMR predictor software, running on a Gateway Pentium 4 CPU with a 2.53 GHz processor.

The kinetic studies were performed in a Pierce (Rockford, IL) Reacti-vap model 18780. A 9 place B-1 aluminum heating block and 2 dram glass vials were used.

The first step in synthesis is epoxidation reaction of methyl oleate, as shown in Scheme 1, using formic acid and hydrogen peroxide to give epoxidized methyl oleate (EMO). This was followed by ring opening reaction of EMO using propionic, levulinic, hexanoic, octanoic, and ethyl hexanoic acid to give respective α-hydroxy ester derivatives of methyl oleate (PMO, LMO, HMO, OMO, EHMO).

Epoxidation of Methyl Oleate

The epoxidation reaction was based on a Swern epoxidation[19,20] which has been modified for oleochemical use by Bunker and Wool[29] and used by our laboratory in the past.[32] First, 420.0 g (1.4 mol) of methyl oleate is placed in a heavy duty separatory funnel type 500 mL roundbottom flask equipped with an overhead stirrer. Next, 15 g (0.3 mol) of formic acid was slowly added forming a layered mixture. The reaction flask was cooled in an ice bath and 254 g of 30% hydrogen peroxide (2.2 mol) is added over about 5 min while monitoring the temperature of the solution. The peroxide was added slowly enough such that the temperature of the solution remained below room temperature. Gas bubbles were evident as the hydrogen peroxide was added. The reaction was allowed to proceed at room temperature and alliquots were taken and analyzed by GC. The reaction was judged to be complete after 5 hrs. The product was purified in the reaction flask by stirring with 100 mL of hexanes and discarding the aqueous/formic acid layer. Then, ~110 mL of saturated sodium bicarbonate solution was stirred with the hexane layer and removed. This sodium bicarbonate washing was repeated leaving the solution slightly basic. The hexane layer was dried over ~80 g of anhydrous sodium sulfate, filtered through a fritted funnel. The hexane was removed with rotary evaporation (~60° C.; overnight). Molecular sieves were added to ensure the product remained dry. The isolated yield was 410 g (1.3 mol: 93% yield).

Kinetic Studies

First, ~1.7 g (0.0054 mol) of EMO was added to a 2 dram vial. Next, ~4 g (0.054 mol, 10 equivalents) of propionic acid was added along with 0, 5, or 10 mol % of the appropriate catalysts studied. The vials were purged with nitrogen sealed with septa, then placed in the Pierce Reacti-vap 19780 at the appropriate temperatures. Aliquots (~20 uL) of each reaction were taken, diluted in 1 mL of acetone, and analyzed by GC. Total reaction time depended upon temperature, and ranged from 6 hrs at 120° C. to 24 hrs at 88° C.

Larger Scale Syntheses

First, a 5 fold or greater excess of the carboxylic acid was used to function as both the reactant and solvent. The carboxylic acid, propanoic (140 g), octanoic (138 g), or 2-ethyl hexanoic acid (138 g), levulinic (138 g) was placed in a 250 mL roundbottom reaction flask or a 500 mL cylindrical reaction vessel equipped with an overhead stirrer. Next, 60 g (0.19 mol) EMO was added. The reaction was heated to 100° C. using an oil bath or heating mantle. The reactions were periodically monitored by injection of aliquots into the GC. The reaction time for complete reaction was ~7 hrs in all of the reactions. All of the products, as well as the hexanoic product were also synthesized in an analogous manner on a ~15 g scale. The products HMO, PMO, and LMO were purified by washing with water (100 mL) 3×. OMO and 2-EHMO were not water washed due to the lower water solubility of the acid starting material in those cases. The residual acid removed first by rotary evaporation at 40° C. then on a Kugel-Rohr evaporator at 70° C. The products were dried over molecular sieves and were characterized by FTIR (FIGS. 1-4), GC, GC-MS, $^1$H and $^{13}$C NMR. The overall percent yields for the syntheses were: PMO 86%, OMO 87%, 2-EHMO 90%, and LMO 62%.

The PMO $^1$H NMR: (500 MHz, CDCl$_3$): δ 4.84 (b, protons on the ester branched carbon of the fatty chain), δ 3.67 (s, 3, protons from methoxy group), δ 3.58 (b, hydroxy proton), δ 2.38 (q, 2, protons on side chain α to carboxy group), δ 2.30 (t, 2, protons α to fatty chain carboxy group), δ 1.16 (t, 3, protons on the end of the side chain), δ 0.88 (t, 3, protons on the end of the fatty chain), urresolvable signals from δ 1.62-1.18. $^{13}$C NMR: (125 MHz, CDCl$_3$) δ 174.4 (carbonyl carbon of branched ester), δ 174.2 (cabonyl carbon of fatty chain), δ 76.4, 76.3, 72.6, 72.5 (oxygen bonded carbons at the 9 and 10 positions of the fatty chain), δ 51.5 (carbon of the methoxide group), δ 34.0-22.6 (multiple signals from fatty carbon chain), δ 14.0 (end carbon of fatty chain), δ 9.2 (end of branched sidechain). The spectral peaks and assignments are close to computed chemical shift and in order.

The HMO $^1$H NMR: (500 MHz, CDCl$_3$): δ 4.84 (b, protons on the ester branched carbon of the fatty chain), δ 3.68 (s, 3, protons from methoxy group), δ 3.59 (b, hydroxy proton), δ 2.3-2.31 (m, 4, protons on side chain α to both carboxy groups), δ 0.90 (m, 6, protons on the end of the fatty chain and the side chain), urresolvable signals from δ 1.63-1.27. $^{13}$C NMR: (125 MHz, CDCl$_3$) δ 174.3 (cabonyl carbon of fatty chain), δ 173.8 (carbonyl carbon of branched ester), δ 76.3, 76.2, 72.6 (oxygen bonded carbons at the 9 and 10 positions of the fatty chain), δ 51.4 (carbon of the methoxide group), δ

34.5-22.3 (multiple signals from fatty carbon chain), δ 14.1 (end carbon of fatty chain), δ 13.9 (end of branched sidechain). The spectral peaks and assignments are close to computed chemical shift and in order.

The OMO $^1$H NMR: (500 MHz, CDCl$_3$): δ 4.84 (b, protons on the ester branched carbon of the fatty chain), δ 3.67 (s, 3, protons from methoxy group), δ 3.59 (b, hydroxy proton), δ 2.38 (q, 2, protons on side chain α to carboxy group), δ 2.31 (t, 2, protons α to fatty chain carboxy group), δ 1.16 (t, 3, protons on the end of the side chain), δ 0.89 (t, 3, protons on the end of the fatty chain), urresolvable signals from δ 1.62-1.27. $^{13}$C NMR: (125 MHz, CDCl$_3$) δ 174.3 (cabonyl carbon of fatty chain), δ 173.7 (carbonyl carbon of branched ester), δ 76.4, 76.3, 72.6 (oxygen bonded carbons at the 9 and 10 positions of the fatty chain), δ 51.4 (carbon of the methoxide group), δ 34.0-22.7 (multiple signals from fatty carbon chain), δ 14.1 (end carbon of fatty chain), δ 9.3 (end of branched sidechain). The spectral peaks and assignments are close to computed chemical shift and in order.

The 2-EHMO $^1$H NMR: (500 MHz, CDCl$_3$): δ 4.76 (b, protons on the ester branched carbon of the fatty chain), δ 3.59 (s, 3, protons from methoxy group), δ 3.52 (b, hydroxy proton), δ 2.8 (unresolved m, 3, protons on side chain α to both carboxy groups), δ 0.81 (unresolved m, 9, protons on the end of the fatty chain and side chain), urresolvable signals from δ 1.62-1.27. $^{13}$C NMR: (125 MHz, CDCl$_3$) δ 176.2 (carbonyl carbon of branched ester), δ 174.3 (cabonyl carbon of fatty chain), δ 76.2, 76.0, 72.5, 72.4 (oxygen bonded carbons at the 9 and 10 positions of the fatty chain), δ 51.8 (carbon of the methoxide group), δ 34.2-22.6 (multiple signals from fatty carbon chain), δ 14.2 (end carbon of fatty chain), δ 11.9 (end of branched sidechain). The spectral peaks and assignments are close to computed chemical shift and in order.

The LMO $^1$H NMR: (500 MHz, CDCl$_3$): δ 4.84 (b, protons on the ester branched carbon of the fatty chain), δ 3.67 (s, 3, protons from methoxy group), δ 3.59 (b, hydroxy proton), δ 2.31 (m, 4, protons on side chain α to both carboxy groups), δ 2.78 (d, 2, protons on carbon 2 of the side chain α to ester linkage), δ 2.59 (d, 2, protons on carbon 3 of the side chian α to the ketone), δ 2.20 (s, 3, protons on the end of the side chain), δ 0.89 (t, 3, protons on the end of the fatty chain), urresolvable signals from δ 1.62-1.27. $^{13}$C NMR: (125 MHz, CDCl$_3$) δ 206.9 (ketone carbonyl of side chain), δ 174.3 (carbonyl carbon of branched ester), δ 172.7 (cabonyl carbon of fatty chain), δ 72.7, 72.5 (oxygen bonded carbons at the 9 and 10 positions of the fatty chain), δ 51.5 (carbon of the methoxide group), δ 38.2 (carbon 3 of the side chain α to the ketone), δ 34.1-22.6 (multiple signals from fatty carbon chain), δ 14.0 (end carbon of fatty chain). Additionally the minor product could be identified by a $^1$H NMR resonance at δ0 2.45 (proton on carbon α to carboxylic acid), and $^{13}$C NMR resonances: α 177 (acid carbonyl of side chain) and δ 108.3 (ketal carbon). The spectral peaks and assignments are close to computed chemical shift and in order.

The GC-MS of all of the samples showed similar trends. The molecular ions were not observed in any of the sample, as expected for EI ionization. Large peaks were observed at m/Z=155 and 187, which have been observed for epoxidized methyl fatty materials, and assigned to a fragment with fatty chain cleavage between the 9 and 10 carbons, and the 10 and 11 carbons respectively.[33-35] As expected, the retention time of the compounds on the GC-MS increased with increasing molecular weight.

Results and Discussion

We performed the straightforward epoxidation of methyl oleate, which went as expected. As in previous studies performed in our laboratory, the reaction was closely monitored by GC to avoid the synthesis of the undesired 9,10-dihydroxystearate which will form if the reaction temperature is elevated or the reaction is allowed to progress for too long.

The ring opening to form the ester derivatives was a simple straightforward reaction as well (Scheme 1). In all of the reaction cases, we monitored the reaction progress closely by taking aliquots of the reaction solution and analyzing them by GC.

The products were identified, and structure was confirmed by FTIR and NMR analysis. The FTIR spectra of the starting material and product in the PMO reaction, (FIG. 1) show the loss of the epoxide bands from ~827~840 cm$^{-1}$, and the corresponding increase in the ester carbonyl at ~1740 cm$^{-1}$ confirming the ester structure of the product. Additionally, an increase in the absorbance at ~3500 cm$^{-1}$ was also evident, as expected for the OH group. The FTIR of three of the other products (FIGS. 2-3), OMO, HMO (not shown), and 2-EHMO display similar features. In LMO FTIR spectra, (FIG. 4), an additional overlapping carbonyl peak at 1718 cm$^{-1}$ is also observable.

Both $^{13}$C NMR and $^1$H NMR analysis of the products also confirms the reaction. In the $^{13}$C NMR of the product, a new carbonyl signal at ~178 is evident and the signal for the epoxide carbons at δ 51 is absent. There is also a resonance at δ 207 in the LMO system, corresponding to the product ketone. The loss of the signal from the protons on the epoxy carbons, in the 9 and 10 positions of the fatty chain, at δ2.85 is also observable in the $^1$H NMR, with a corresponding increase in peaks at ~δ4.8 and ~δ3.6. Resonances from the carbon side chain that are in the α-position to the ester, are also observable.

Of additional interest was the identification of a minor cyclic ketal product (Scheme 2) in the product mixture. This product was identified by the characteristic $^{13}$C NMR resonances at δ177 and δ108 of the free acid carbonyl carbon and the ketal carbon respectively. Similar compounds have been synthesized and have received consideration for use as lubricants and fuel lubricity enhancers.[36]

Figure 5:
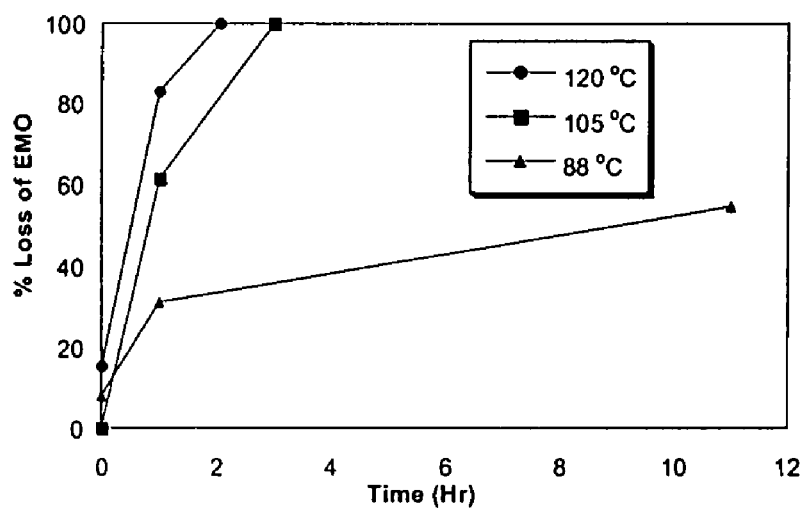
FIG. 5 shows the ring opening reaction progress followed by the loss of EMO starting material as monitored by GC analysis from Example 1.
Figure 6:
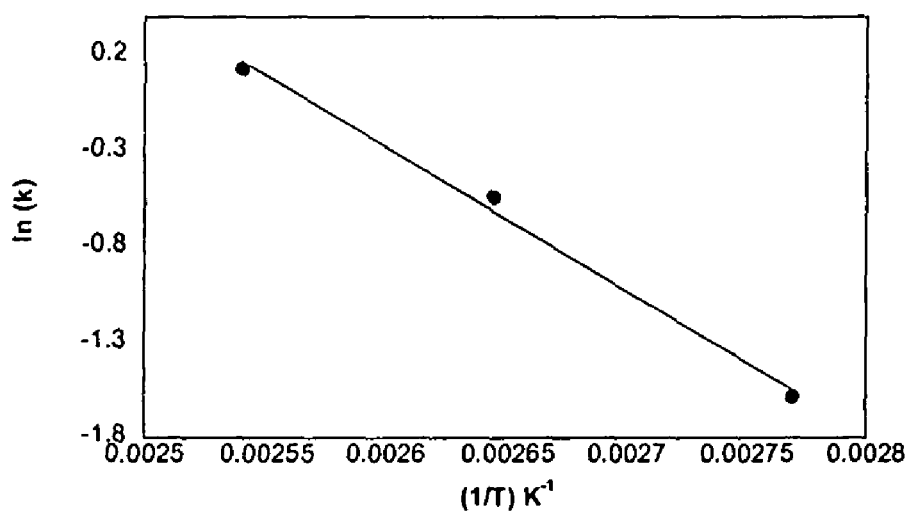
FIG. 6 shows an Arrhenius plot of the catalyst free reaction over the temperature range studied from Example 1. From the slope of this line, (−7519.6 K) an activation energy of 62.5 kJ mol$^{-1}$ (14.94 kcal mol$^{-1}$) can be calculated.

Further insight into this reaction was gained by a careful study of the propionic acid system. We chose to use the reactant, propionic acid, in 10 fold excess to allow our reaction to follow pseudo first order kinetics. We studied this reaction at three different temperatures 120, 105, and 88° C. giving us a 32 degree temperature range of data. As expected the reaction was considerable faster at higher temperature (FIG. 5) and was complete in less than 2 hours. Using the data from the initial phase of the reaction, pseudo $1^{st}$ order rate constants of 1.1, 0.59, and 0.21 hr$^{-1}$ were calculated for the reactions at 120, 105, and 88° C. respectively, which lead to corresponding $t_{1/2}$s of 0.63, 1.27, and 3.3 hrs. These numbers were used to make an Arrhenius plot (FIG. 6) and calculate an activation energy for the reaction of 62.5 kJ mol$^{-1}$ (14.94 kcal mol$^{-1}$). A literature comparison of this activation energy[37] shows it to be in the expected range of 51-66 kJ mol$^{-1}$ for epoxide ring opening. Additionally, our activation energy is nearly identical to the ab initio calculated value of 60.7 kJ mol$^{-1}$ (14.5 kcal mol$^{-1}$) for the ring opening of an epoxide through an inversion transition state without cationic assistance.[38] Our values are also in the range of values, 57.7-69.1 kJ mol$^{-1}$ (13.7-16.5 kcal mol$^{-1}$) found for the ring opening of the epoxidized vegetable oils under various conditions.[39]

We looked for the possible increase in the reaction rate of our system with added cationic assistance. The catalyst studied included LiBr, KBr, TBABr, and NaOH in both 5 and 10 mol %. Only the LiBr showed rate enhancement which was quite small. The maximum pseudo first order rate constant of 1.39 hr$^{-1}$ at 120° C. was only about a 20% increase over the uncatalyzed rate. Due to this small enhancement, we did not use catalyst in any of our syntheses of branched oleochemicals.

Figure 7:
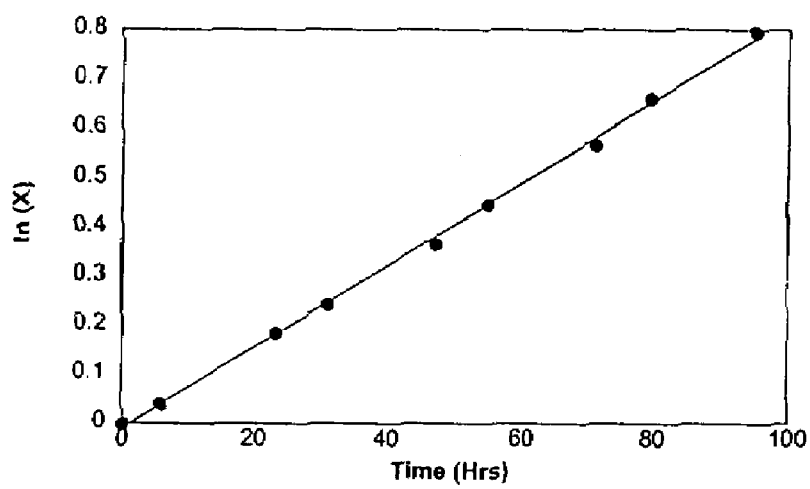
FIG. 7 shows a kinetic plot of ln (X) vs time to obtain the second order rate constant for the ring opening esterification of EMO in butanol solvent; X=([EMO]$_{initial}$[propionic acid])/ ([propionic acid]$_{initial}$[EMO]) from Example 1. The second order rate constant can be obtained from a slope of the line and is 0.0216 M$^{-1}$ hr$^{-1}$.

Because the literature claimed a possible effect of salvation on the reaction rate[38], we also performed our reaction in the solvent, butanol due to its convenient boiling point and ability to solubilize all of the reagents. The reaction was performed at 100° C. and monitored by GC as in the pseudo first order cases. From this reaction, a second order rate constant of 0.0216 M$^{-1}$ hr$^{-1}$ can be calculated from the kinetic plot (FIG. 7). For comparison to the pseudo first order data and the second order data, a value of 12.2 M for the concentration of propionic acid can be used which gives a rate constant of 0.28 hr$^{-1}$ at 100° C. This is in good agreement with the data conducted under the pseudo first order conditions, and demonstrates the there is no significant rate enhancement or reduction caused by solvent in the system.

We have demonstrated the synthesis of potentially useful oleochemical derivatives from the methyl oleate and simple carboxylic acids using a simple epoxidation reaction followed by a ring opening esterification. Research on these compounds has shown interesting lubricity and pour-point properties. We have also identified a minor ketal product in one of our systems. The branched oleochemicals may find use in the surfactant, lubricant, and fuel additive industries.

EXAMPLE 2

Materials and Methods

The α-hydroxy ester derivatives of methyl oleate (PMO, LMO, HMO, OMO, EHMO) were preepared as described in Example 1.

Viscosity Measurements

Brookfield viscosity: The dynamic viscosity at 25° C. was measured on a Brookfield (Middleboro, Mass.), DV-III programmable Rheometer controlled by Rheocalc 2.4 software. It was equipped with a CP-40 spindle and programmed to vary the sheer rate from 0.5-10 RPM. The viscosity was determined by the software using a Bingham model. In this model, the viscosity is found from the slope of a shear rate vs. shear stress relationship. An experiment was also performed varying the shear stress instead of the shear rate, and the results were identical. The temperature of the system was controlled by a Brookfield (Middleboro, Mass.) TC-602 water bath.

Kinematic Viscosity: The kinematic viscosity of various hydroxy ester derivatives of methyl oleate was measured using Cannon-Fenske calibrated viscometers (Cannon Instrument Co., State College, Pa.) in a Cannon temperature bath (CT-1000) at 40 and 100° C., as per ASTM D445-95 method. The viscosities obtained are average values of 2-3 determinations and the precision is with in the limits of ASTM method specification.

Oxidation Stability

Pressure Differential Scanning Calorimetry (PDSC): The experiments were carried out using a PC controlled DSC 2910 thermal analyzer from TA Instruments (New Castle, USA. A small amount of sample (typically 1.5-2.0 mg) was placed in a hermetically sealed type aluminum pan with a pinhole lid for interaction of the sample with the reactant gas (extra dry air). The controlled diffusion of the gas through the hole greatly restricts the volatilization of the oil while still allowing for saturation of the liquid phase with air. A film thickness of less than 1 mm was required to ensure proper oil-air interaction and eliminate any discrepancy in the result due to gas diffusion limitations. The module was first calibrated for baseline, and then for temperature using the melting point of indium metal (156.6° C.) at 10° C./min heating rate. Extra dry air was pressurized in the module at a constant pressure of 1379 KPa (200 PSI) and a scanning rate of 10° C./min was used throughout the experiment. The onset temperature (OT) of oxidation was calculated from the exotherm in each case.

Thin Film Micro Oxidation (TFMO): A small amount of oil (25 µl) was oxidized as a thin film on a high carbon steel catalyst surface of pans with a steady flow (20 ml/min) of dry air. These pans were placed on heated aluminum slab lying on a hot plate. The temperature was maintained with in ±1° C. This arrangement eliminated temperature gradient across the aluminum surface, transferred uniform heat to the pans placed on the slab. The pans were covered by a bottomless glass reactor. Oxidation tests were done at 150, 175, 200, and 225° C. for 120 min. The constant air flow ensured removal of volatile oxidation products. The test was designed to eliminate any gas diffusion limitation. After oxidation, the pan containing the oxidized oil sample was removed from the oxidation chamber and cooled rapidly under a steady flow of dry nitrogen and transferred to a desiccator for temperature equilibration. After 2 h, the catalyst containing the oxidized oil was weighed to determine the volatile loss (or gain) due to oxidation and then soaked (30 min) with tetrahydrofuran (THF) to dissolve the soluble portion of the oxidized oil. After dissolving the soluble portion of the oxidized oil, the pan was dried and weighed to determine the remaining insoluble deposit.

Pour Point and Cloud Point

Pour points and cloud points were measured as per the ASTM D-5949 and ASTM D-5773 method respectively using Phase Technology Analyzer, Model 70X (Phase technology, Hammersmith Gate, Richmond, B.C., Canada). The pour point is defined as the temperature in ° C. when the sample still pours when the jar is tilted. Statistically the method has shown quite good consistency for determining low temperature flow property of fluids.

Tribological Behavior

Ball-on-disk: Boundary lubrication properties of hydroxy ester derivatives of methyl oleate were studied using ball-on-disk configuration on a multi-specimen friction measurement apparatus of Falex (Sugar Grove, IL). Ball-on-disk experiments (1018 steel disk, Rc 15-25) were carried out for 30 min under low speed 6.22 mm/sec (5 rpm) and high load 181.44 kg (1779 N) at 25° C. using 0.01M concentration of samples in hexadecane. Measurements of coefficient of friction (CoF) and torque were made in each case. The CoF values reported are averages of two or three independent experiments and the standard deviation observed was ±0.02.

Four-Ball: The experiment is designed to study the anti-wear properties of samples under sliding contact by four-ball test geometry using a Falex apparatus (Model Multi-Specimen, Falex Corporation, Sugar Grove, IL). The test zone is a top ball rotating in the cavity of three identical balls in contact and clamped in a cup below, containing the test fluid. Three balls are clamped together and make three-point contact with the top ball. The resistance to the motion of the ball is measured by a load cell connected to the stationary cup on the load platform, containing the 3 balls. Appropriate load is applied from below and the top ball is rotated at a set speed for a particular length of time. The balls (52100 steel, 12.7 mm diameter, 64-66 Rc hardness and extreme polish) were thoroughly cleaned with methylene chloride and hexane before each experiment. Fifteen ml of test fluid (5 wt % samples in base oils such as soybean oil SBO, polyalphaolefin PAO4, and hexadecane HD) was poured in the test cup to cover the stationary balls. The test sequence for PAO solutions allowed the speed to attain a set rpm of 1200 before a normal load of 40 Kg (392 N) was applied at room temperature for 15 minutes. For SBO and HD solutions, the test sequence was same except for the speed, which was 2400 rpm. Temperature of the test fluid was 22° C. which increased to 27-28° C. at the end of the 15 min run. Wear scar diameter on balls were measured using a digital optical microscope. Two measurements, perpendicular to each other, were recorded for each scar on a ball and the average of six measurements for three balls was taken in each case. The scar-diameter is reported in millimeters. The standard deviation of six measurements was less than 0.04 in all the experiments. Duplicate tests were done with new set of balls and the scar diameter varied within ±0.04 mm.

Results and Discussion

Synthesis of α-hydroxy ester derivatives from EMO, shown in scheme 1, is an effective way of introducing branching on the fatty acid (FA) chain. The reaction is a one-pot reaction and the final product has significantly improved low-temperature, thermo-oxidative stability and friction wear properties compared with EMO.

Viscosity

The physicochemical properties of EMO, PMO, LMO, OMO, EHMO and HMO are presented in Table 1. The dynamic viscosity of the products was measured by a Brookfield rheometer at 25° C., while the kinematic viscosity was measured by Cannon-Fenske method at 40 and 100° C. Kinematic and dynamic viscosity of LMO is significantly higher than the other products. This is due to more polar structure of LMO compared with HMO, OMO and EHMO, that results in stronger intermolecular interaction. This property of LMO would translate into enhanced lubricity in a dynamic system. With the exception of LMO, the viscosities increase with increasing chain length of ester branching. This can be rationalized by an overall increase in the molecular weights of the products with increasing chain length of newly added ester group.

Low Temperature Fluidity

The pour point and cloud point measurements provide a good estimate low-temperature fluidity of the lubricants. The low-temperature fluidity of vegetable oils is extremely poor and this limits their use in subzero temperatures. At low temperatures, vegetable oils have a tendency to form macro crystalline structures through uniform stacking of the 'bend' triacylglycerol backbone. Branching on fatty acid chains may disrupt this stacking process and results in improved low temperature properties. This approach is used here to improve the low-temperature flow behavior of fatty acid esters by attaching ester branching at the double bond sites. Attachment of an ester side chain with optimum length at the epoxy carbons improves the pour point significantly. EMO has pour point of 0° C. and cloud point of 3.9° C. Except LMO, the other products with ester branching have pour point in the range of −15 to −33° C. and cloud points in the range −8 to −31° C. The introduction of levulinic acid side chain did not make significant improvement in the cold flow behavior, possibly due to polar structure, which also led to increased viscosity. Attachment of octanoic acid has significantly decreased the pour point and cloud point to −33 and −31° C. respectively. It can be assumed that the presence of a branching attached to the fatty acid ester does not allow individual molecules to come close for easy stacking due to steric interactions, and thus inhibiting crystallization, resulting in lower pour and cloud point.

Friction and Wear Properties

Figure 8:
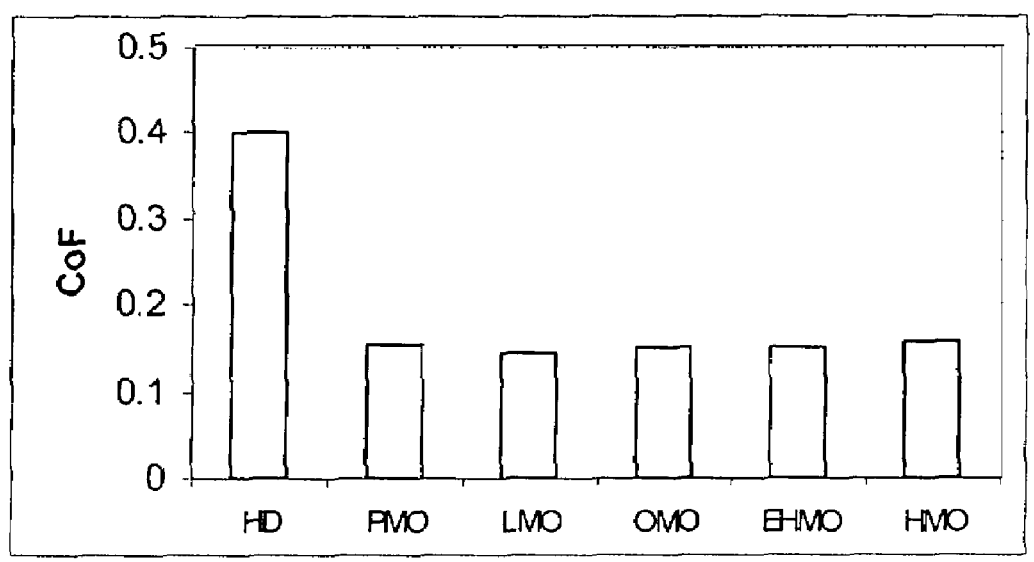
FIG. 8 shows the coefficient of friction data on 0.01 M concentrations of hydroxy ester products in hexadecane (HD) obtained using Ball-on-disk configuration under conditions: load 400 lb, speed 5 rpm, ambient temperature, time 30 min from Example 2.

An important property of the lubricants is their ability to maintain a stable lubricating film at the metal contact zone. Vegetable oils and fatty acid esters are known to provide excellent lubricity due to their ester functionality. The ester ends of the fatty acid chain attach to metal surfaces, thus permitting monolayer film formation with the hydrocarbon end of fatty acids sticking away from the metal surface. The fatty acid chain thus offers a sliding surface that prevents the direct metal to metal contact. If the film is not formed, direct metal contact may result in high temperatures at the contact zones of moving parts causing adhesion, scuffing or even metal-to-metal welding. Under lubricated condition, the hydroxy and ester group of the products offers active oxygen sites that provide better adsorption to the metal surface. The friction reducing property of hydroxy ester products as additives in hexadecane is demonstrated by the coefficient of friction (CoF) obtained using ball-on-disk experiment. The results are shown in FIG. 8. Under a high load of 181.44 kg and low speed 6.22 mm s-1 (5 rpm), all of the hydroxy ester products show excellent reduction in CoF at 0.01M concentration. The CoF values of all products are less than 0.15 and are a considerable improvement over neat hexadecane (0.4). Even at such low concentration, these compounds are reducing the CoF to a great extent, thereby acting as friction reducing additives. The CoF values are also lower than the values using methyl oleate as an additive, 0.19[40] and EMO as an additive in hexadecane, 0.22[41] at the same concentration.

Figure 9:
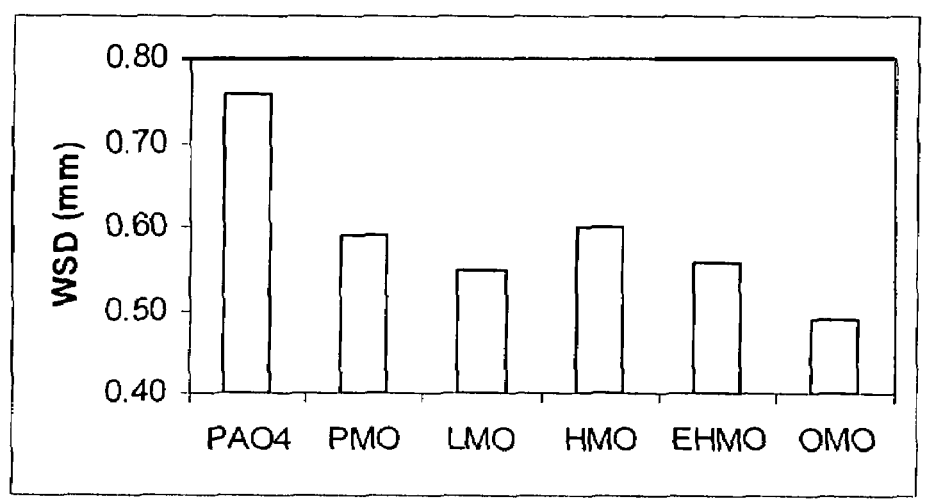
FIG. 9 shows the four-ball wear scar diameters (WSD) on 5% solutions of hydroxy ester products in PAO4 under conditions: load 88 lb, speed 1200 rpm, room temperature, time 15 min from Example 2.
Figure 10:
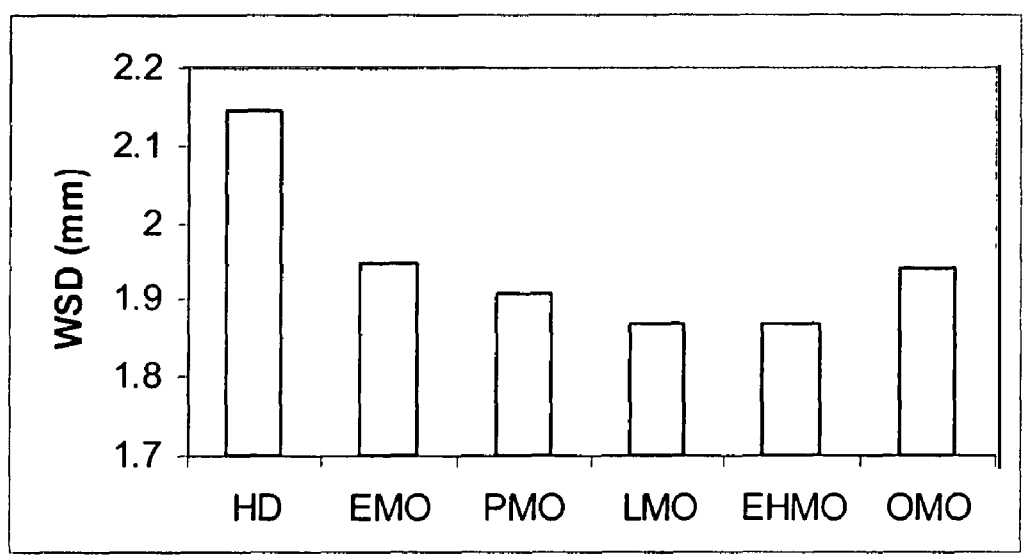
FIG. 10 shows the four-ball wear scar diameters (WSD) on 5% solutions of hydroxy ester products in hexadecane (HD) under conditions: load 88 lb, speed 2400 rpm, room temperature, time 15 min from Example 2.
Figure 11:
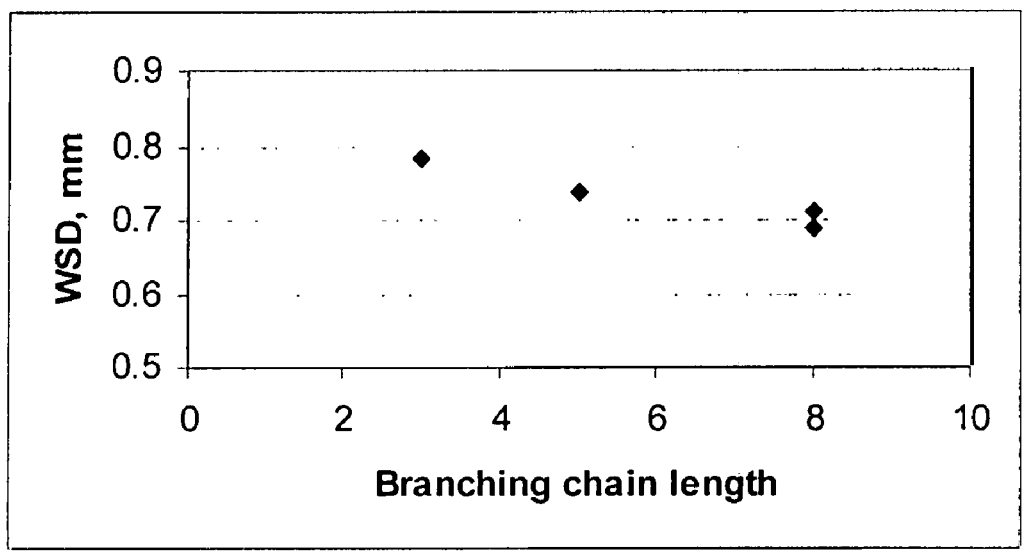
FIG. 11 shows the four-ball wear scar diameters (WSD) on 5% solutions of hydroxy ester products in SBO as a function of branching chain length under conditions: load 88 lb, speed 2400 rpm, room temperature, time 15 min from Example 2.

The four ball test's were done in three different base oils, hexadecane (HD), soybean oil (SBO), and polyalphaolefin (PAO4) to demonstrate their effectiveness in petroleum, bio and synthetic base oils. These base oils did not contain any additives. Hydroxy ester products (PMO, LMO, HMO, OMO, EHMO) were introduced into base oils at 5% concentration. Under the normal four ball conditions, i.e. speed of 1200 rpm, the addition of the hydroxy ester products as additives in PAO4 show lower wear scar diameter than PAO4 itself (FIG. 9). Even at a high speed of 2400 rpm also, the ester hydroxy products at 5% level, reduced the wear scar diameter of hexadecane (FIG. 10). The addition of hydroxy ester products causes considerable wear reduction in PAO4 and hexadecane. Overall, as the branching chain length increases, the wear scar diameter decreases, as shown for 5% solutions in SBO in FIG. 11. One possible reason is increased viscosity due to increase in molecular weight as a result of long branchings.

A possible explanation for improved tribological properties of hydroxy ester products is that there are two extra polar functional groups apart from ester group of fatty acid ester. Oxygen moeties like hydroxy and ester functionality at 9, 10 position on fatty acid help the compounds adhere to the metal surface and reduce friction, especially under load. The active functional groups of these compounds start acting during the metal rubbing process. During this time, these molecules undergo chemical transformation at the metal contact zone and develop a stable tribochemical film to protect further wear of the metal. These compounds demonstrate excellent antifriction and antiwear properties using ball-on-disk and four ball test geometry respectively.

Thermo-Oxidative Stability

Differential scanning calorimeter (DSC) is one of the useful techniques in evaluating the effect of temperature on properties of materials. These changes are represented as exothermic or endothermic peaks as a function of temperature. In general, exothermic peaks are due to the chemical decomposition and oxidation, while endothermic peaks are due to physical processes such as melting, boiling and transition, etc.

Pressure DSC (PDSC) is an effective way of measuring the oxidative tendency of lubricant base oils, vegetable oils and oleochemicals in an accelerated mode[42, 43, 44]. At high air pressure (1379 kPa), the concentration of oxygen is in excess and at equilibrium with the sample. Thus, any inconsistency due to access rate of oxygen and egress rate of volatile degradation product is effectively eliminated. The OT is the temperature at which a rapid increase in the rate of oxidation is observed and obtained by extrapolating the tangent drawn on the steepest slope of reaction exotherm to the baseline. A high OT would suggest a high oxidation stability of the oil. Here, we compared the stabilities of the hydroxy ester products. The OT for PMO is highest (175° C.) among this series of hydroxy ester products, followed by EHMO (166° C.), LMO (162° C.), and OMO (160° C.). The PMO shows high oxidative stability compared with others. The data shows that oxidative stability decreases with increase in chain length of ester side chain. This is due to the fact that longer side chains are more susceptible to oxidation cleavage than short compact ones. The results are corroborated by another study on chemically modified vegetable oils[45] as well as synthetic esters[46] wherein the authors mentioned that short-chain acids are more stable than long-chain acids.

Another oxidation test was conducted using TFMO to study volatility and deposit forming tendencies of hydroxy ester products. In most of the lubricant applications, lubricating conditions are thin film, so TFMO test is considered a test of choice to simulate the actual conditions where oxygen diffusion is not limiting[44]. This is also suitable for quantitative evaluation of lubricants thermal and oxidative stability, because of its good correlation with the PDSC method and the time consuming rotary bomb oxidation test. During the oxidation process, some primary oxidation products are small fragments of the molecules and are lost as volatile loss, while the others in presence of excess oxygen undergo further oxypolymerization reaction to form oil insoluble deposit. Unsaturated oleochemicals have a higher tendency to form such deposit, which is the main detrimental factor for their use in high-temperature lubricants. The volatile loss obtained from TFMO tests may be used to predict the useful life of lubricants, as it provide the information about the amount of base fluid left for lubrication. The amount of oil left in the lubricant after TFMO is present in the form of un-oxidized oil, polar oxidation products and polymerized products.

Figure 12:
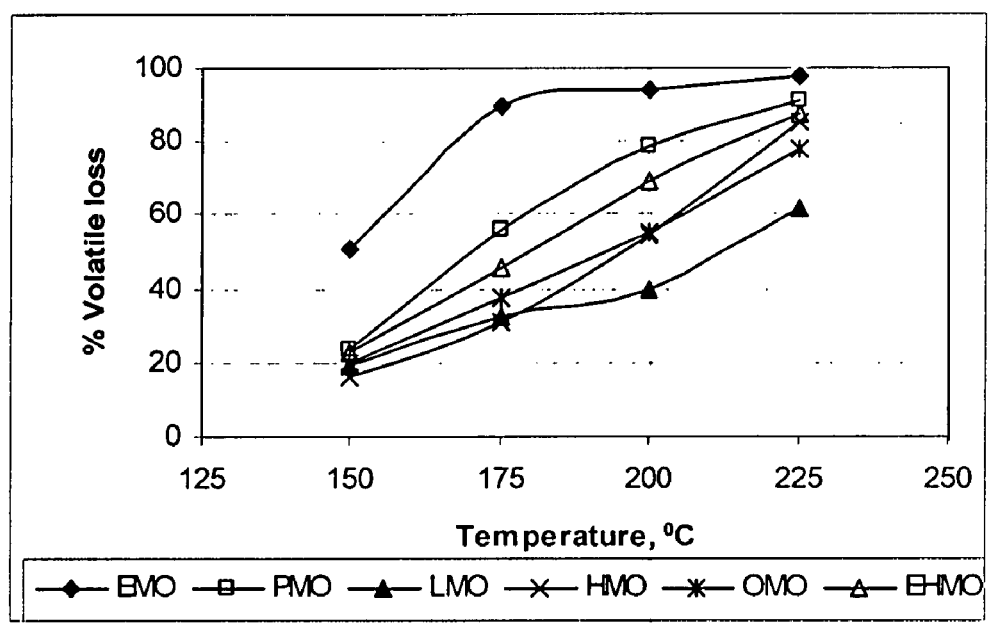
FIG. 12 shows the volatile loss for EMO and its hydroxy ester derivatives, obtained using TFMO at various temperatures from Example 2.

Microoxidation was carried out on EMO and various hydroxy ester products at different temperatures. FIG. 12 presents the volatile loss obtained at different temperatures using TFMO with air. The volatile loss increases consistently as the temperature is increased from 150 to 225° C. in 25° C. increments. This indicates that breakdown of hydroxy ester products as a result of oxidative degradation increases with temperature and reaching the maximum at 225° C., while for EMO the maximum reaches at 175° C. Even at 150° C., volatile loss for EMO (50%) is 2-2.5 times higher than hydroxy ester products.

Figure 13:
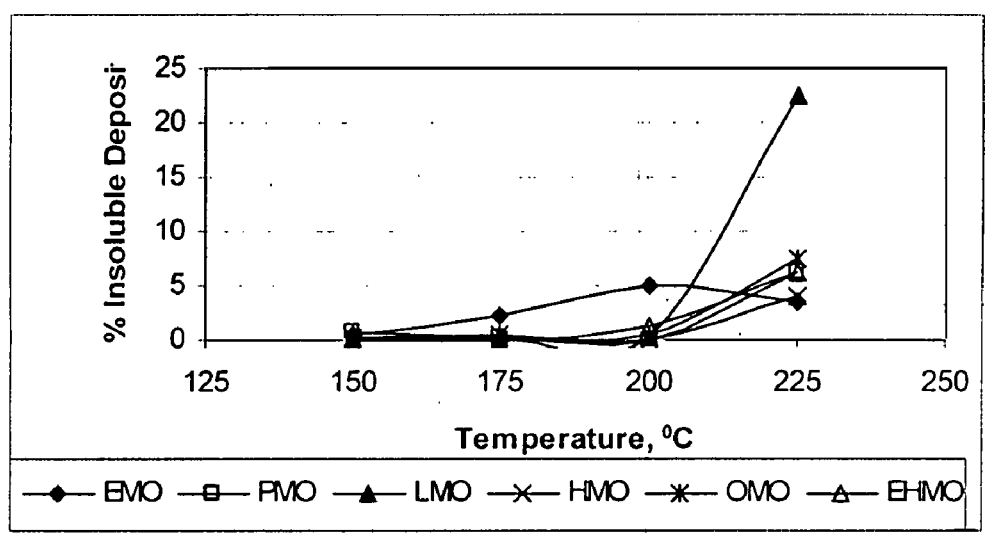
FIG. 13 shows the TFMO insoluble deposit for EMO and its hydroxy ester derivatives at various temperatures from Example 2.

The insoluble deposits obtained during TFMO at various temperatures are shown in FIG. 13. The conversion of EMO to hydroxy ester products resulted in low volatile loss as well as negligible insoluble deposit up to 200° C. during oxidation process. This suggests no significant oxidative degradation occurs up to 200° C. for all hydroxy ester products, and are stable to deposit formation tendency. Thereafter, a small increase in the deposit formation (4-6%) is noted for hydroxy ester products except LMO (23%). This suggests that after 200° C., breakdown of the molecules lead to oxidative polymerization through the generation of reactive oxygen radicals. The percent insoluble deposit for EMO becomes stable after 200° C. The following sharp increase in the deposit formation of LMO after 200° C. suggests a rapid breakdown and increased oxidative polymerization. This is due to the presence of carbonyl group in LMO that serves as additional site for reaction at higher temperature with primary oxidation products resulting in more polymerization (leading to more insoluble deposits) and less volatile product formation.

Conclusions

The results show that under some conditions, hydroxy ester products have better lubricant properties which enable them to outperform their methyl ester analogues. Additionally, they maintain the advantages inherent from their biobased nature. These products remain a viable option for application in the lubricant industry. The following conclusions can be drawn:

(1) Hydroxy ester products as additives in hexadecane possess good antifriction properties demonstrated using ball-on-disk configuration.
(2) These products show good antiwear properties compared with various neat base oils such as PAO4, hexadecane, and soybean oil.
(3) One of the hydroxy ester products, OMO, demonstrates excellent low temperature properties, while others show good low temperature fluidity compared to their methyl ester.
(4) Overall, the hydroxy ester products have good thermo-oxidative stability shown by low volatile loss and insoluble deposit compared with epoxy methyl oleate.
(5) For this series of hydroxy ester products, the viscosity and antiwear properties increase, and pour point and cloud point decrease with increase in chain length of branching.

In conclusion, these hydroxy ester products have shown the dual function of improving low temperature fluidity as well as an effective antifriction and antiwear additive in various lubrication system.

It is understood that the foregoing detailed description is given merely by way of illustration and that modifications and variations may be made therein without departing from the spirit and scope of the invention.

Scheme 1

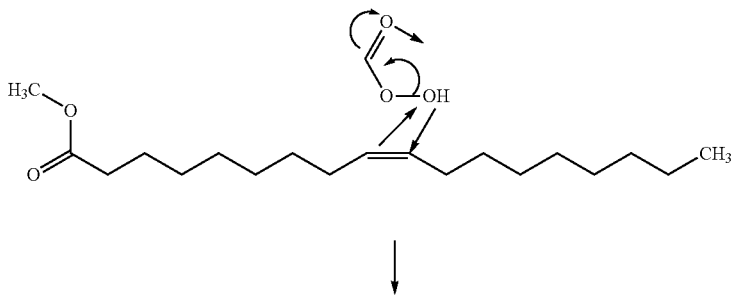

-continued
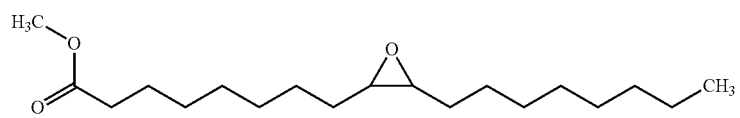
Epoxidized Methyl Oleate (EMO)
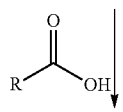
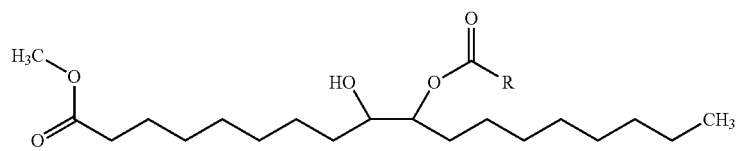
methyl hydroxy-oleate ester derivatives
(LMO, PMO, HMO, OMO, 2-EHMO)
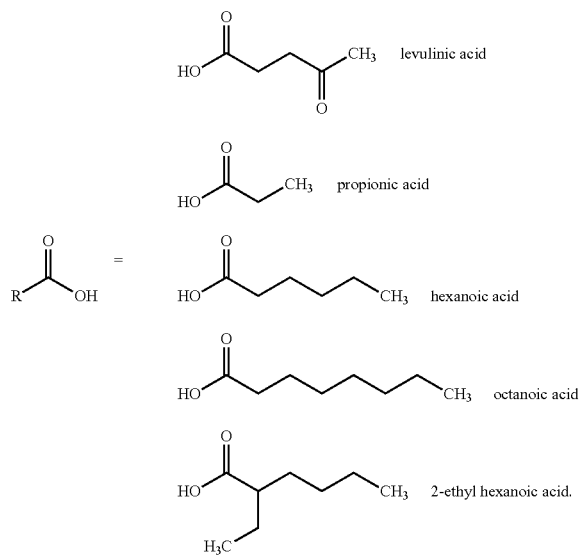
Scheme 2
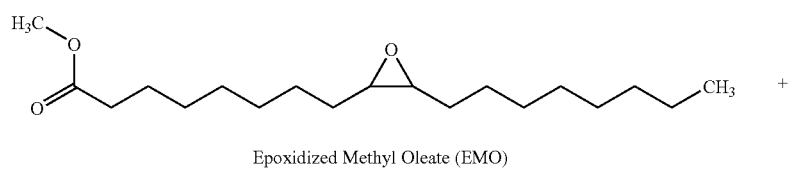
Epoxidized Methyl Oleate (EMO)

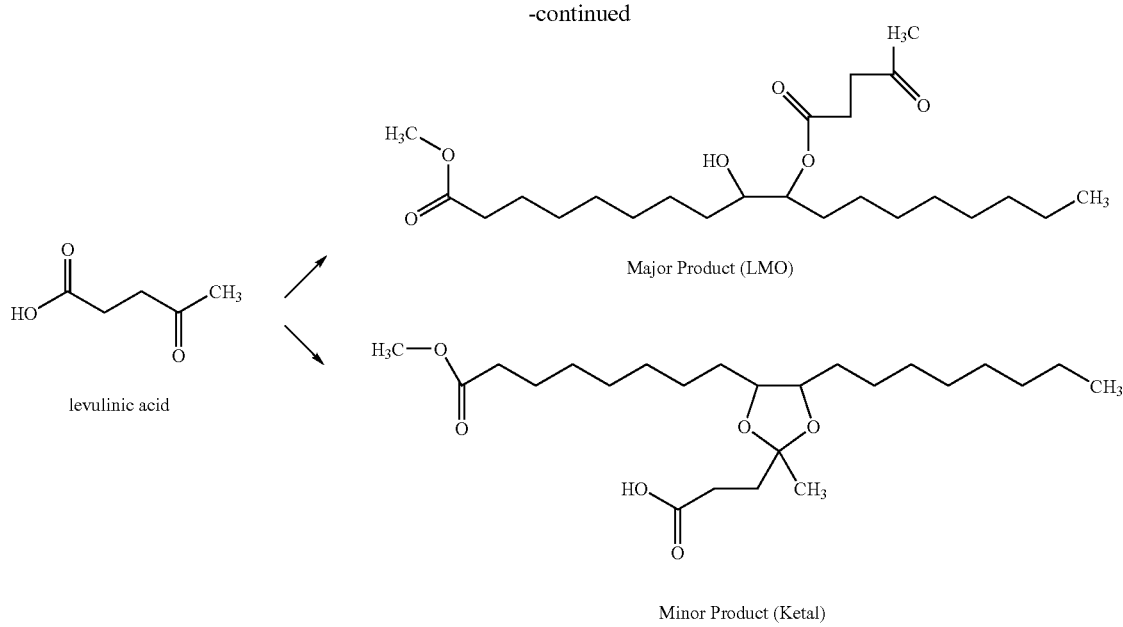

Major Product (LMO)

Minor Product (Ketal)

levulinic acid

References
(1) Van Arnum, P., Analysts Say Oil at $50 Per Barrel Is Possible. *Chemical Market Reporter* 2004, 266, (6), 1-2.
(2) Viswanathan, P., Oil Price Threat. *Chemical Market Reporter* 2005, 267, (12), 1.
(3) Erhan, S. Z.; Adhvaryu, A.; Liu, Z. Chemically Modified Vegetable Oil-based Industrial Fluid. U.S. Pat. No. 6,583,302 B1, Jun. 24, 2003, 2003.
(4) Hwang, H.-S.; Erhan, S. Z., Modification of epoxidized soybean oil for lubricant formulations with improved oxidative stability and low pour point. *J. Am. Oil Chem. Soc.* 2001, 78, (12), 1179-1184.
(5) Hwang, H.-S.; Erhan, S. Z., Lubricant Base Stocks from Modified Soybean Oil. In *Biobased Industrial Fluids and Lubricants*, ed.; Erhan, S. Z.; Perez, J. M., AOCS Press: Champaign, 2002; 20-34.
(6) Hwang, H.-S.; Adhvaryu, A.; Erhan, S. Z., Preparation and properties of lubricant basestocks from epoxidized soybean oil and 2-ethylhexanol. *J. Am. Oil Chem. Soc.* 2003, 80, (8), 811-815.
(7) Hillion, G.; Proriol, D., Synthesis of a high-grade lubricant from sunflower oil methyl esters. *OCL—Oleagineux Corps Gras Lipides* 2003, 10, (5-6), 370-372.
(8) Pollock, C. M.; Nelson, L. A. Fatty acid esters and uses thereof. US2005/0075254A1, Apr. 7, 2005, 2005.
(9) Stiriba, S.-E.; Kautz, H.; Frey, H., Hyperbranched molecular nanocapsules: Comparison of the hyperbranched architecture with the perfect linear analogue. *J. Am. Chem. Soc.* 2002, 124, (33), 9698-9699.
(10) Istratov, V.; Kautz, H.; Frey, H.; Kim, Y.-K.; Schubert, R., Linear-dendritic nonionic poly(propylene oxide)-polyglycerol surfactants. *Tetrahedron* 2003, 59, (22), 4017-4024.
(11) de Guzman, D., Importance of Oleochemical Emphasized at World Surfactants Congress. *Chemical Market Reporter* 2004, 266, (1), 14.
(12) Johansson, I.; Svensson, M., Surfactants based on fatty acids and other natural hydrophobes. *Current Opinion in Colloid & Interface Science* 2001, 6, (2), 178-188.
(13) De Caro, P. S.; Mouloungui, Z.; Gaset, A., Synthesis of derivatives of alkylamino alkyloxy propanol structures by N-alkylation, acylation, and nitration. Application as fuel additives. *J. Am. Oil Chem. Soc.* 1997, 74, (3), 241-247.
(14) Aramaki, K.; Khalid, H. M., Effect of addition and molecular size of triglyceride oils on phase behavior and surfactant self-assemblies. *Journal of Oleo Science* 2004, 53, (11), 557-563.
(15) Rosen, M. J.; Dahanayake, M., *Industrial Utilization of Surfactants: Principles and Practice*. ed.; AOCS Press: Champaign, Ill., 2000.
(16) Rosen, M. J., *Surfactants and Interfacial Phenomena*. 3rd. ed.; John Wiley and Sons, Inc.: Hoboken, 2004.
(17) Rosen, M. J.; Mathias, J. H.; Davenport, L., Aberrant aggregation behavior in cationic gemini surfactants investigated by surface tension, interfacial tension, and fluorescence methods. *Langmuir* 1999, 15, (21), 7340-7346.
(18) Kjellin, U. R. M.; Reimer, J.; Hansson, P., An investigation of dynamic surface tension, critical micelle concentration, and aggregation number of three nonionic surfactants using NMR, time-resolved fluorescence quenching, and maximum bubble pressure tensiometry. *J. Colloid Interface Sci.* 2003, 262, (2), 506-515.
(19) Findley, T. W.; Swern, D.; Scanlan, J. T., Epoxidation of Unsaturated Fatty Materials with Peracetic Acid in Glacial Acetic Acid Solution. *J. Am. Chem. Soc.* 1945, 67, 412-414.
(20) Schmits, W. R.; Wallace, J. G., Epoxidation of Methyl Oleate with Hydrogen Peroxide. *J. Am. Oil Chem. Soc.* 1954, 31, 363-365.
(21) La Scala, J.; Wool, R. P., Effect of FA composition on epoxidation kinetics of TAG. *J. Am. Oil Chem. Soc.* 2002, 79, 373-378.
(22) Crocco, G. L.; Shum, W. F.; Zajacek, J. G.; Kesling, H. S. J. Epoxidation Process. 5166372, Nov. 24, 1992, 1992.
(23) Poh, B. T.; An, E. K., Mooney scorch time and cure index of epoxidized natural rubber in presence of sodium carbonate. *J. Appl. Polym. Sci.* 2001, 82, (6), 1352-1355.
(24) Poh, B. T.; Tan, B. K., Mooney scorch time of epoxidized natural rubber. *J. Appl. Polym. Sci.* 1991, 42, (5), 1407-1416.

(25) Liu, Z. S.; Erhan, S. Z.; Xu, J.; Calvert, P. D., Development of soybean oil-based composites by solid freeform fabrication method: Epoxidized soybean oil with bis or polyalkyleneamine curing agents system. *J. Appl. Polym. Sci.* 2002, 85, (10), 2100-2107.

(26) Liu, Z. S.; Erhan, S. Z. In *Development of Soybean Oil-based Energy Absorbing Materials*, The United States-Japan Cooperative Program in Natural Resources Food and Agricultural Panel., Tsukuba, Ivaraki, Japan, Nov. 9-147, 2003, 2003; 'Ed.'^'Eds.' Tsukuba, Ivaraki, Japan, 2003; p^pp 394-400.

(27) La Scala, J.; Wool, R. P., Rheology of chemically modified triglycerides. *J. Appl. Polym. Sci.* 2005, 95, (3), 774-783.

(28) Khot, S. N.; Lascala, J. J.; Can, E.; Morye, S. S.; Williams, G. I.; Palmese, G. R.; Kusefoglu, S. H.; Wool, R. P., Development and application of triglyceride-based polymers and composites. *J. Appl. Polym. Sci.* 2001, 82, (3), 703-723.

(29) Bunker, S. P.; Wool, R. P., Synthesis and characterization of monomers and polymers for adhesives from methyl oleate. *J. Polym. Sci., Part A: Polym. Chem.* 2002, 40, 451-458.

(30) Warwel, S.; Brüse, F.; Schier, H., Glucamine-based gemini surfactants I: Gemini surfactants from long-chain N-alkyl glucamines and diepoxides. *J. Surfact. Deterg.* 2004, 7, (2), 181-186.

(31) Warwel, S.; Brüse, F., Glucamine-based gemini surfactants II: Gemini surfactants from long-chain N-alkyl glucamines and epoxy resins. *J. Surfact. Deterg.* 2004, 7, (2), 187-193.

(32) Doll, K. M.; Erhan, S. Z., Synthesis of carbonated fatty methyl esters using supercritical carbon dioxide. *J. Agric. Food Chem.* 2005, 53, (24), 9608-9614.

(33) Plattner, R. D.; Gardner, H. W.; Kleiman, R., Chemical Ionization Mass Spectrometry of Fatty Acids: The Effect of Functional Groups on the CI Spectra. *J. Am. Oil Chem. Soc.* 1983, 60, (7), 1298-1303.

(34) Carlson, K. D.; Kleiman, R.; Bagby, M. O., Epoxidation of lesquerella and limnanthes (meadowfoam) oils. *J. Am. Oil Chem. Soc.* 1994, 71, (2), 175-182.

(35) Orellana-Coca, C.; Adlercreutz, D.; Andersson, M. M.; Mattiasson, B.; Hatti-Kaul, R., Analysis of fatty acid epoxidation by high performance liquid chromatography coupled with evaporative light scattering detection and mass spectrometry. *Chem. Phys. Lipids* 2005, 135, (2), 189-199.

(36) Filley, J., New lubricants from vegetable oil: Cyclic acetals of methyl 9,10-dihydroxystearate. *Bioresource Technology* 2005, 96, (5), 551-555.

(37) Campanella, A.; Baltanás, M. A., Degradation of the oxirane ring of epoxidized vegetable oils with solvated acetic acid using cation-exchange resins. *Eur. J. Lipid Sci. Technol.* 2004, 106, (8), 524-530.

(38) Harder, S.; Van Eikema Hommes, N. J. R.; Von Ragué Schleyer, P.; Van Lenthe, J. H., Nucleophilic ring opening of epoxides by organolithium compounds: Ab initio mechanisms. *J. Am. Chem. Soc.* 1994, 116, (6), 2508-2514.

(39) Campanella, A.; Baltana?s, M. A., Degradation of the oxirane ring of epoxidized vegetable oils in liquid-liquid systems: II. Reactivity with solvated acetic and peracetic acids. *Lat. Am. Appl. Res.* 2005, 35, (3), 211-216.

(40) Kurth T L, Sharma B K, Doll K M, Erhan S Z. Chemical Engineering Communications 2006; submitted

(41) Sharma B K, Doll K M, Erhan S Z. New Journal of Chemistry 2007; submitted.

(42) Dunn R O. Fuel Processing Technology 2005; 86(10): 1071-85.

(43) Zhang Y Y, Ren T H, Wang H D, Yi M R. Lubrication Science 2004; 16(4):385-92.

(44) Adhvaryu A, Sharma B K, Hwang H S, Erhan S Z, Perez J M. Ind. Eng. Chem. 2006; 45(3):928-33.

(45) Sharma B K, Adhvaryu A, Liu Z, Erhan S Z. J. Am. Oil Chem. Soc. 2006; 83(2):129-36

(46) Randals S J, in, Synthetic Lubricants and High Performance Functional Fluids, Rudnick L R, Shubkin R L (Eds.). Marcel Dekker, New York, 1999, p. 63-102.

We claim:

1. A method of making fatty acid ester derivatives comprising:

reacting in the presence of an acid catalyst an epoxidized fatty acid or an ester thereof having one or more oxirane rings of the formula:

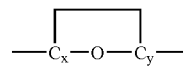

wherein x and y are consecutive integers, with a first carboxylic acid of the formula R—COOH to form (a) a hydroxy fatty acid ester derivative wherein said oxirane ring is opened and converted to a hydroxy ester of the formula:

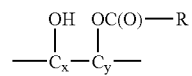

in combination with (b) a fatty acid ketal wherein said oxirane ring is opened and converted to a ketal group of the formula:

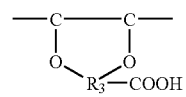

wherein said R of said first carboxylic acid is a ketone or aldehyde of the formula $R_3(O)$ wherein said $R_3$ is selected from the group consisting of cyclic, straight or branched chain hydrocarbons, and substituted cyclic, straight or branched chain hydrocarbons.

2. The method of claim 1 further comprising producing said epoxidized fatty acid or an ester thereof by reacting an unsaturated fatty acid or an ester thereof having one or more sites of unsaturation —$C_x$=$C_y$—, wherein x and y are consecutive integers, with an epoxidation reagent to form said fatty acid epoxide wherein at least one of said sites of unsaturation of said fatty acid or fatty acid ester is converted to said oxirane ring.

3. The method of claim 2 wherein said unsaturated fatty acid ester is of the formula $R_1$—COO$R_2$ wherein $R_1$ is a straight or branched chain olefin, and $R_2$ is selected from the group consisting of H, branched or straight chain alkyl or alkenyl groups, aromatic containing groups, and glycerides.

4. The method of claim 2 wherein said epoxidation reagent is selected from the group consisting of a peroxide with a carboxylic acid, a peroxide with a carboxylic acid anhydride, and a peroxy-carboxylic acid.

5. The method of claim 4 wherein said epoxidation reagent is selected from the group consisting of a peroxide and formic acid, a peroxide and acetic acid, a peroxide and acetic anhydride, and peroxy-benzoic acid.

6. The method of claim 2 wherein said epoxidation reagent comprises a peroxide and a carboxylic acid or a carboxylic acid anhydride, and further wherein said peroxide and said carboxylic acid or said carboxylic acid anhydride are mixed prior to said reacting with said unsaturated fatty acid.

7. The method of claim 2 wherein said epoxidation reagent comprises a peroxide and a carboxylic acid or a carboxylic acid anhydride, and further wherein said peroxide and said carboxylic acid of said carboxylic acid anhydride are mixed concurrently with said reacting with said unsaturated fatty acid.

8. The method of claim 2 wherein said reacting said unsaturated fatty acid with said epoxidation reagent is conducted at a temperature between about 0° C. and about 30° C.

9. The method of claim 2 wherein said unsaturated fatty acid is selected from the group consisting of oleic acid, linoleic acid, linolenic acid, palmitoleic acid, erucic acid, 5-eicosenoic acid, 5-docosenoic acid, 5,13-docosadienoic acid, petroselinic acid, and alkyl esters thereof.

10. The method of claim 2 wherein said unsaturated fatty acid comprises oleic acid or alkyl esters thereof.

11. The method of claim 1 wherein said first carboxylic acid comprises levulinic acid and said fatty acid ketal is of the formula:

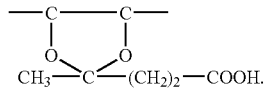

12. The method of claim 1 wherein said reacting said epoxidized fatty acid or ester thereof with said first carboxylic acid is conducted at a temperature below about 120° C.

13. The method of claim 12 wherein said reacting said epoxidized fatty acid or ester thereof with said first carboxylic acid is conducted at a temperature below about 100° C.

* * * * *